US009645062B2

(12) United States Patent
Gere

(10) Patent No.: US 9,645,062 B2
(45) Date of Patent: May 9, 2017

(54) ROOFING PULL-TEST FRAME ASSEMBLY

(71) Applicant: Duro-Last, Inc., Saginaw, MI (US)

(72) Inventor: Keith Allan Gere, Frankenmuth, MI (US)

(73) Assignee: Duro-Last, Inc., Saginaw, MI (US)

( * ) Notice: Subject to any disclaimer, the term of this patent is extended or adjusted under 35 U.S.C. 154(b) by 0 days.

(21) Appl. No.: 14/682,706

(22) Filed: Apr. 9, 2015

(65) Prior Publication Data
US 2015/0292997 A1    Oct. 15, 2015

Related U.S. Application Data

(60) Provisional application No. 61/978,396, filed on Apr. 11, 2014.

(51) Int. Cl.
| | | |
|---|---|---|
| *G01L 5/04* | (2006.01) | |
| *G01N 3/08* | (2006.01) | |
| *G01M 5/00* | (2006.01) | |
| *G01L 5/00* | (2006.01) | |

(52) U.S. Cl.
CPC ............ *G01N 3/08* (2013.01); *G01M 5/0075* (2013.01); *G01L 5/0033* (2013.01); *G01L 5/04* (2013.01); *G01N 2203/0003* (2013.01); *G01N 2203/0017* (2013.01)

(58) Field of Classification Search
CPC ......... G01L 5/003; G01L 5/0033; G01L 5/04; G01N 2203/0003; G01N 2203/0017; G01N 3/08; E02D 33/00; G01M 5/0075

USPC ............ 73/761, 786, 826, 827, 828, 862.01, 73/862.381, 862.391–862.393, 862.542, 73/862.584, 150 A, 150 R, 848, 851, 845, 73/842, 838, 834
See application file for complete search history.

(56) References Cited

U.S. PATENT DOCUMENTS

| | | | | |
|---|---|---|---|---|
| 3,797,301 A * | 3/1974 | Hawes | ................... | E02D 1/022 346/33 R |
| 3,942,368 A * | 3/1976 | Hoyt | ..................... | G01L 5/0033 73/784 |
| 4,046,000 A * | 9/1977 | Watkins | ................... | G01N 3/08 73/817 |
| 4,662,227 A * | 5/1987 | Peterson | .................. | G01N 3/00 73/826 |
| 4,753,115 A * | 6/1988 | Moody | ..................... | G01N 3/08 73/826 |
| 5,792,961 A * | 8/1998 | Giebner | ................... | G01N 3/08 73/786 |
| 6,848,322 B2 * | 2/2005 | Scarborough | ............ | G01N 3/20 73/850 |
| 7,175,368 B2 * | 2/2007 | Stotzer | ..................... | E02D 33/00 405/232 |
| 7,260,998 B2 * | 8/2007 | Madden | ..................... | G01L 5/24 73/761 |

(Continued)

*Primary Examiner* — Jonathan Dunlap
(74) *Attorney, Agent, or Firm* — Reising Ethington P.C.

(57) ABSTRACT

A roofing pull-test frame assembly includes a base, a frame plate, and legs. The base is placed on a roof during use of the roofing pull-test frame assembly. The base has one or more walls with a bracing surface. The legs extend between the base and the frame plate and support the frame plate above the base when the roofing pull-test frame assembly is assembled together. In use, loads experienced during a pull-testing event are transmitted between the legs and base via surface-to-surface abutment with the bracing surface.

11 Claims, 5 Drawing Sheets

(56) References Cited

U.S. PATENT DOCUMENTS

| | | | | |
|---|---|---|---|---|
| 7,441,471 B1* | 10/2008 | Davis | ........................ | E02D 7/22 |
| | | | | 405/303 |
| 7,513,168 B2* | 4/2009 | Alba | ........................ | G01N 3/16 |
| | | | | 73/818 |
| 8,402,837 B1* | 3/2013 | Jones | .................. | G01M 5/0058 |
| | | | | 73/788 |
| 8,534,139 B2* | 9/2013 | Huang | .................... | G01N 19/04 |
| | | | | 73/150 A |
| 9,341,600 B2* | 5/2016 | Cavaliero | ................. | G01L 1/04 |
| 9,360,397 B1* | 6/2016 | Melton | ............... | G01M 99/007 |
| 2005/0074297 A1* | 4/2005 | Stoetzer | ................. | E02D 33/00 |
| | | | | 405/233 |
| 2006/0207337 A1* | 9/2006 | Madden | ..................... | G01L 5/24 |
| | | | | 73/761 |
| 2014/0360283 A1* | 12/2014 | Kawka | ................ | G01M 5/0075 |
| | | | | 73/837 |

\* cited by examiner

ROOFING PULL-TEST FRAME ASSEMBLY

CROSS-REFERENCE TO RELATED APPLICATION

This application claims the benefit of U.S. Provisional Patent Application No. 61/978,396, filed on Apr. 11, 2014, the entire contents of which are hereby incorporated by reference.

TECHNICAL FIELD

The present disclosure generally relates to roofing installations, and more particularly relates to roofing pull-test frame assemblies employed for conducting a pull-test to a roof.

BACKGROUND

In some roofing installations, a membrane is adhered over top an existing and aging roof. This saves the effort, time, and money associated with demolishing the existing roof and disposing of its remains, and in this way presents a more environmentally sustainable alternative. The existing roof commonly includes a roof deck made of concrete, wood, or metal, and includes several layers on top of the roof deck containing a mix of asphalt, insulation, heavy felt paper, and/or granules. Still, existing roofs can include other constructions. Before a membrane is adhered to an existing roof, however, the existing roof should be inspected to be sure that it is suitable for repurposing and need not be replaced altogether. Part of that inspection typically involves determining the strength and structural integrity of the existing roof and that of an adhered joint between the membrane and an exposed surface of the existing roof.

Pull-testing is the usual procedure employed to observe these strengths and structural integrities. A test area of the existing roof is prepared with a sample membrane adhered to the exposed surface and a piece of wood adhered over the membrane. A pull-test frame is placed on the existing roof at the prepared test area. A pull plate is attached to the piece of wood, and a connected chain leads from the pull plate to a puller and a pressure reader set on an upper part of the frame. The puller draws the pull plate upward with force directed away from the existing roof until failure occurs. The construction of the existing roof can come apart, or the sample membrane can be pulled off of the exposed surface. Whichever occurs first, the pressure reader determines and displays the pressure value at which failure took place.

To date, the pull-test frames can be bulky and unwieldy, and are not always easily carried to the test area and assembled together.

SUMMARY

In one embodiment, a roofing pull-test frame assembly includes a base, a frame plate, and two or more legs. The base is placed on a roof and has one or more wall(s) with a bracing surface. The legs extend between the base and frame plate, and they support the frame plate above the base when the roofing pull-test frame assembly is put together. When put in use, loads that are experienced during a pull-testing event are transmitted from the frame plate, to the legs, and to the wall(s) of the base. The legs transmit the loads by way of surface-to-surface abutment with the bracing surface of the wall(s).

In another embodiment, a roofing pull-test frame assembly includes a base, a frame plate, and a leg. The base has a first bottom wall, a second bottom wall, a first side wall, and a second side wall. The first and second bottom and side walls intersect at a corner of the base. The leg extends between the base and the frame plate, and supports the frame plate above the base when the roofing pull-test frame assembly is assembled together. In assembly and use, the leg extends to the corner of the base and a terminal end surface of the leg makes surface-to-surface abutment with bracing surfaces of the first and second bottom walls. And in assembly and use, an outside surface of the leg makes surface-to-surface abutment with bracing surfaces of the first and second side walls.

DETAILED DESCRIPTION

The figures illustrate an embodiment of a roofing pull-test frame assembly 10 that is used in a pull-testing event. Some pull-testing events are conducted on an existing roof construction that can include a roof deck made of concrete, wood, or metal, and can further include layers on top of the roof deck containing a mix of asphalt, insulation, heavy felt paper, and/or granules. Still, existing roofs can include other constructions. On an existing roof construction, pull-testing is employed to determine the strength and structural integrity of the construction and that of an adhered joint between an added membrane and an exposed surface of the existing roof. The roofing pull-test frame assembly 10 is suitable for use in these types of pull-tests, as well as in pull-testing in other circumstances like for a new roof construction. Compared to some previously-known pull-test frames, the roofing pull-test frame assembly 10 is more handy and easier to assemble and use, and transmits loads more efficiently and effectively. Furthermore, while illustrated by one embodiment in the figures, the roofing pull-test frame assembly 10 can have different designs, constructions, and components in other embodiments, some of which are described below. Indeed, its exact design, construction, and components may depend on the particular application such as the particular pull-test conducted and the particular puller and pressure reader used with the pull-test frame assembly.

Figure 6:
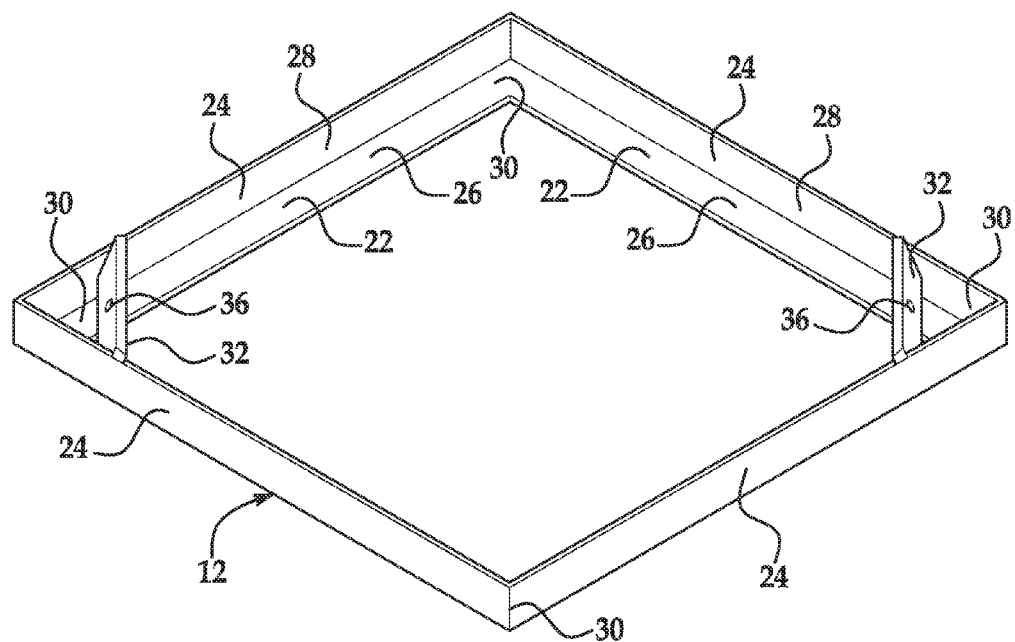
FIG. 6 is a perspective view of a base of the roofing pull-test frame assembly.

Referring generally to FIGS. 1-4, the roofing pull-test frame assembly 10 is made up of multiple components including—in this embodiment—a base 12, a frame plate 14, legs 16, a pull plate 18, and a chain 20. The components are separate and discrete and can be composed of metal materials such as steel and aluminum materials. The base 12 serves as the lower piece of the roofing pull-test frame assembly 10 and is placed directly on the roof subjected to pull-testing. Referring to FIG. 6, the base 12 has a generally square shape that, in one specific example, measures approximately sixteen inches in length and approximately sixteen inches in width; other shapes and measurements are possible. In the embodiment presented by the figures, its shape includes four bottom walls 22 and four side walls 24. The bottom and side walls 22, 24 are planar, and are arranged orthogonally with respect to each other. On their upwardly-directed sides relative to the roof, the bottom walls 22 have bracing surfaces 26 that also happen to be upper surfaces of the bottom walls. Similarly, on their inwardly-directed sides relative to the base's square shape, the side walls 24 have bracing surfaces 28 that also happen to be inner surfaces of the side walls. A pair of bottom walls 22 and a pair of side walls 24 come together to define a corner 30 of the base 12. By its shape, there are a total of four corners 30 in the base 12.

The base 12 includes attachment structures 32 at two diametrically opposite corners 30. As perhaps best shown in FIG. 5, one leg 16 is coupled to each attachment structure 32 via a clevis pin 34. In this way, the leg 16 and base 12 are coupleable and decoupleable to and from each other at the corners 30 that are provided with attachment structures 32. Referring back to FIG. 6, each attachment structure 32 is a planar piece extending diagonally between the two side walls 24 that define the particular corner 30. They each have a hole 36 for receiving the clevis pin 34. The exact number of attachment structures 32 may depend on the number of legs 16, and the exact design and construction of each attachment structure may depend on the design and construction of the base 12 and of the legs.

Figure 7:
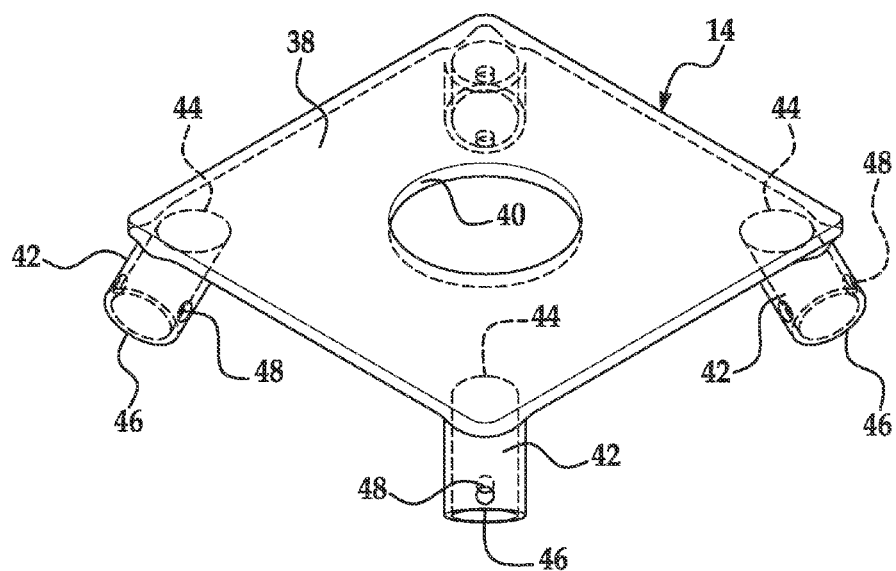
FIG. 7 is a perspective view of a frame plate of the roofing pull-test frame assembly.

The frame plate 14 serves as the upper piece of the roofing pull-test frame assembly 10. The puller and pressure reader that are used during a pull-testing event are set on top of the frame plate 14. Referring to FIG. 7, the frame plate 14 has a plate structure 38 with a generally square shape that, in one specific example, measures approximately eight inches in length and approximately eight inches in width; other shapes and measurements are possible. In this embodiment, a single hole 40 is defined in the middle of the plate structure 38 for accommodating the chain 20 as the chain is pulled during a pull-testing event. The frame plate 14 also has four sleeve structures 42 for coupling to the legs 16. The exact number of sleeve structures 42 may depend on the number of legs 16, and the exact design and construction of each sleeve structure may depend on the design and construction of the legs. In FIG. 7, there are a total of four sleeve structures 42, each one being cylindrical in shape with a hollow interior and extending at an angle from a bottom surface of the plate structure 38. Each sleeve structure 42 has a closed end 44 at the plate structure 38, and has an open end 46 opposite the closed end. Each sleeve structure 42 also has a hole 48 for receiving a clevis pin 50 (FIGS. 1-4). In this way, the frame plate 14 and legs 16 are coupleable and decoupleable to and from each other at the sleeve structures 42. When assembled together, one leg 16 can be inserted into or over one sleeve structure 42 as the sleeve structure receives the leg in an axially overlapping arrangement (the term axially is used here with respect to the cylindrical shape of the sleeve structure).

Figure 8:
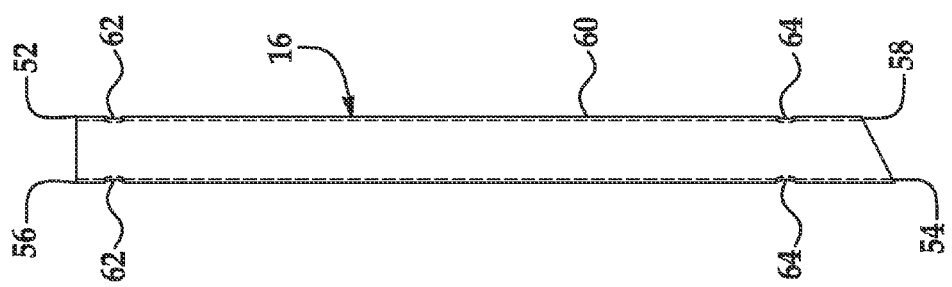
FIG. 8 is a side view of a leg of the roofing pull-test frame assembly.

The legs 16 extend between the base 12 and the frame plate 14 and support the frame plate vertically above the base. The exact number of legs 16 may depend on the design and construction of other components of the roofing pull-test frame assembly 10. For example, in one embodiment there could be two or three legs. Referring to FIG. 8, in this embodiment there are a total of four legs 16, each one being cylindrical in shape with a hollow interior and measuring, in one specific example, approximately twelve inches in axial extent from end-to-end; other shapes and measurements are possible. In this embodiment, each leg 16 has a first open end 52 and a second open end 54. The first open end 52 lies in an imaginary plane that is arranged radially relative to the leg's cylindrical shape and orthogonal to the leg's axial extent (the term axial is used here with respect to the cylindrical shape of the leg). The second open end 54, in contrast, lies in an imaginary plane that is slanted at an angle relative to the leg's axial extent. In one specific example, the second open end 54 is slanted at an angle of approximately sixty-three degrees (63°) relative to the leg's axial extent; other angles are possible. The first open end 52 has a terminal end surface 56, and the second open end 54 has a terminal end surface 58. Each leg 16 has an outside surface 60. Lastly, a first hole 62 is defined completely through both sides of each leg 16 near the first open end 52, and a second hole 64 is likewise defined completely through both sides near the second open end 54. As before, the first hole 62 is for receiving the clevis pin 50, and the second hole 64 is for receiving the clevis pin 34 (FIGS. 1-4). Other techniques for coupling the legs 16 to the base 12 and frame plate 14 are possible in lieu of the clevis pins 34, 50.

Figure 9:
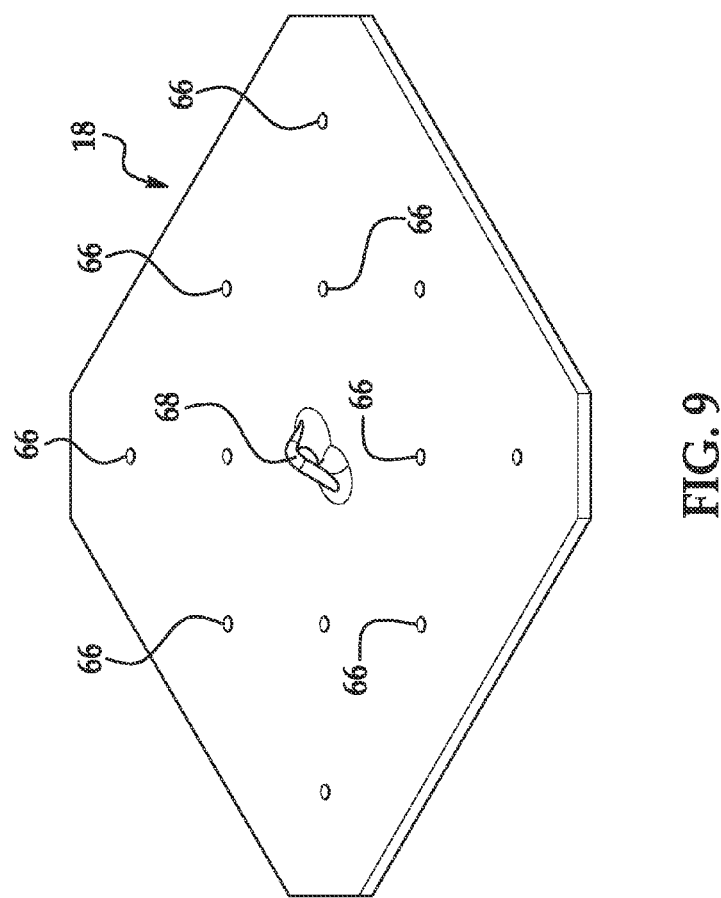
FIG. 9 is a perspective view of a pull plate of the roofing pull-test frame assembly.

The pull plate 18 is attached to the roof either directly or indirectly during a pull-testing event. It is usually attached via fasteners screwed through the pull plate 18 and into the underlying construction. In the embodiment presented by FIG. 9, the pull plate 18 has a generally square shape with its corners severed off so that the pull plate can more readily fit within an interior volume of the roofing pull-test frame assembly 10 roughly defined by the base 12, frame plate 14, and legs 16. Multiple drilled holes 66 are located at different spots in the pull plate 18 for screwing fasteners therethrough, and a handle 68 is located at a center of the pull plate for attachment with the chain 20.

The chain 20 attaches to the pull plate 18 and is connected to the puller and pressure reader used during a pull-testing event. The term chain is used broadly here to refer to metal chains, as well as cords, cables, ropes, and other similar structures and components spanning between the pull plate 18 and the puller and pressure reader.

In one example pull-testing event, a test area of an existing roof is selected and a wood template measuring twelve inches by twelve inches is laid down at the test area. A visible outline of the wood template is drawn directly on an exposed surface of the existing roof. Adhesive is applied to the exposed surface inside of the drawn outline. A cover can be placed around the outside of the drawn outline to preclude the application of adhesive to these areas. A twelve-inch-by-twelve-inch membrane is then placed on top of the adhesive for securing the membrane to the existing roof. The membrane can be a single-ply membrane composed of a thermoplastic material such as a flexible polyvinylchloride (PVC) material having a weft-inserted polyester scrim; these types of membranes are supplied by Duro-Last Roofing, Inc. of Saginaw, Mich. U.S.A. Still, other membranes are possible including one composed of a different material and supplied by a different company. Once in place, the top surface of the membrane can be cleaned with acetone. Adhesive is then applied to the cleaned top surface, and a wood mounting base is placed on top of that adhesive and the adhesive is allowed to cure in order to secure the wood mounting base to the membrane.

Next, the roofing pull-test frame assembly 10 can be put together at the test area. Prior to assembly, the roofing pull-test frame assembly 10 and its components can be in a disassembled state, which in some cases can be easier to transport and carry to the test area compared to an entirely assembled roofing pull-test frame assembly. The legs 16 are coupled to the base 12 and frame plate 14 via the clevis pins 34, 50. The end portion of the legs 16 at the first open end 52 is coupled to the sleeve structures 42, and the end portion of the legs at the second open end 54 extends to the base 12. Where the attachment structures 32 are present at the base 12, the legs 16 are coupled to them. The legs 16 at the base corners 30 that lack the attachment structures 32 can simply abut against the walls 22, 24, as perhaps illustrated best in FIG. 3. This assembly is then placed around the secured wood mounting base and membrane. A visible outline of the base 12 is drawn on the exposed surface of the existing roof at the inside of the base. This visible outline roughly traces the periphery of the wood mounting base at a distance spaced from the periphery. The existing roof can then be cut via a saw down to its underlying roof deck at the visible outline. Resulting roof debris is removed. The pull plate 18 is fastened to the wood mounting base, and the chain 20 is connected to the puller and pressure reader set on top of the frame plate 14. The puller is actuated until failure occurs within the construction of the existing roof itself, or until failure occurs at the membrane/roof securement. Of course, other example pull-testing events are possible including ones with more, less, or different steps than those set forth here.

Figure 1:
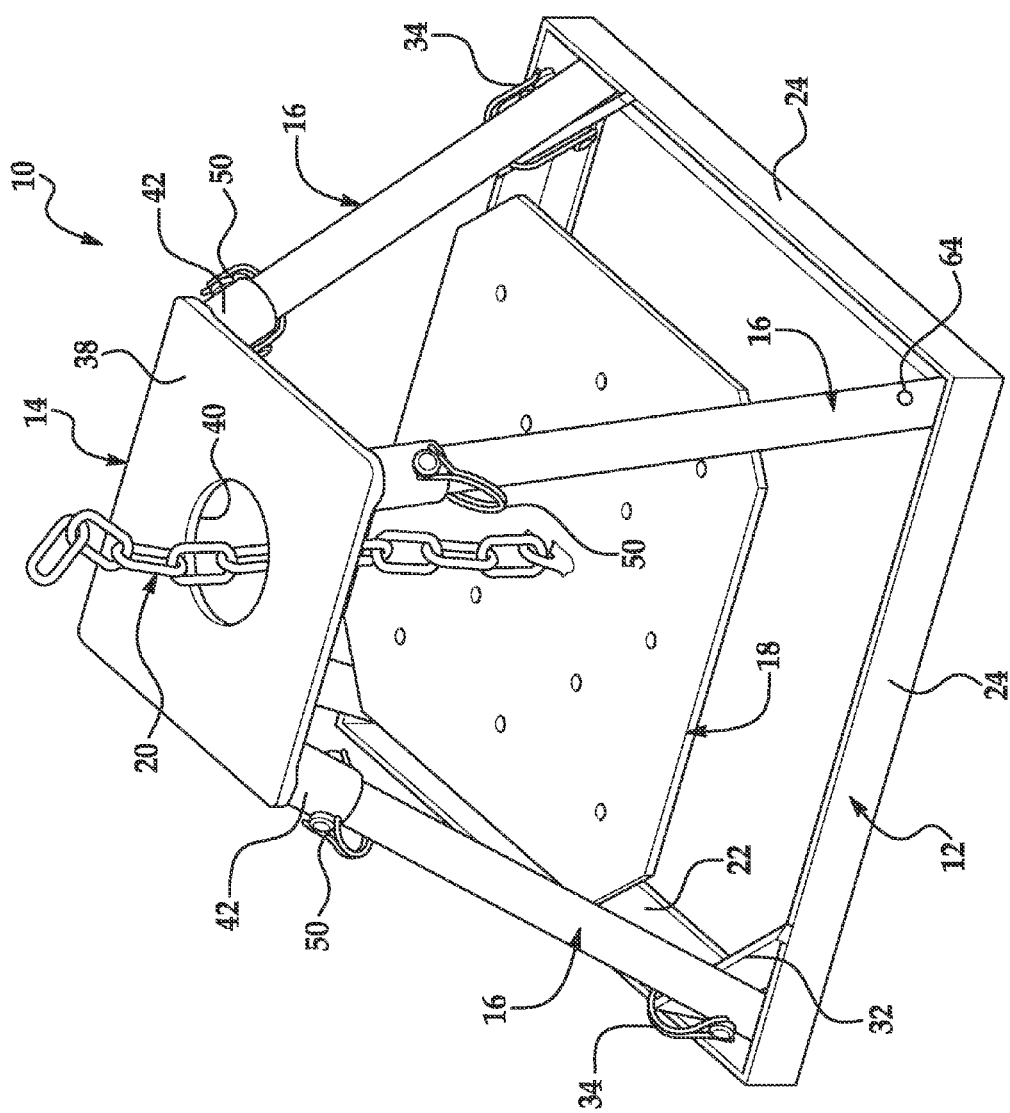
FIG. 1 is a perspective view of a roofing pull-test frame assembly.
Figure 2:
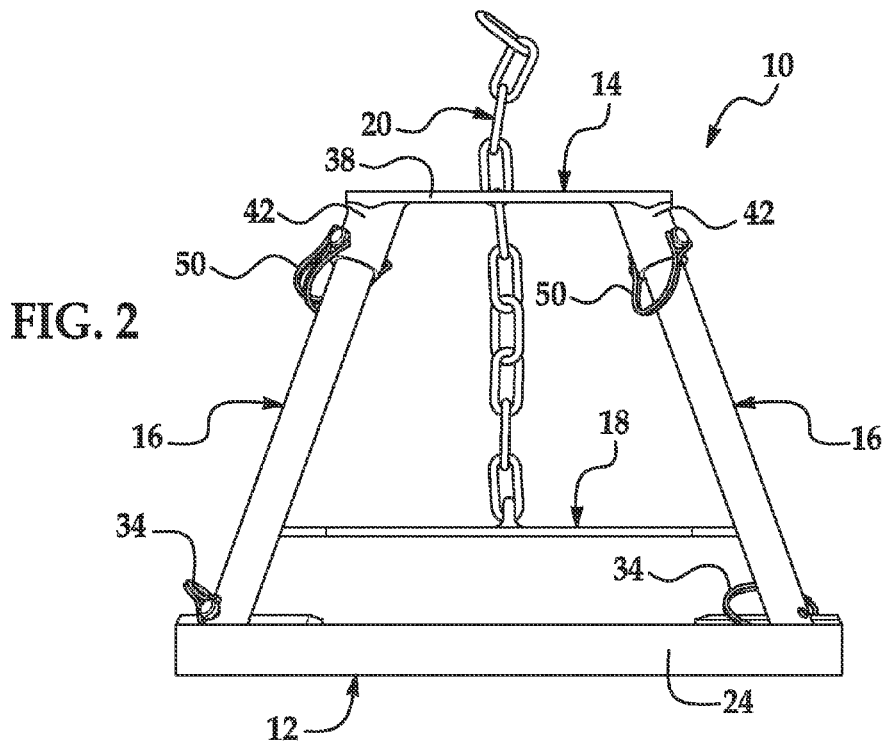
FIG. 2 is a side view of the roofing pull-test frame assembly.
Figure 3:
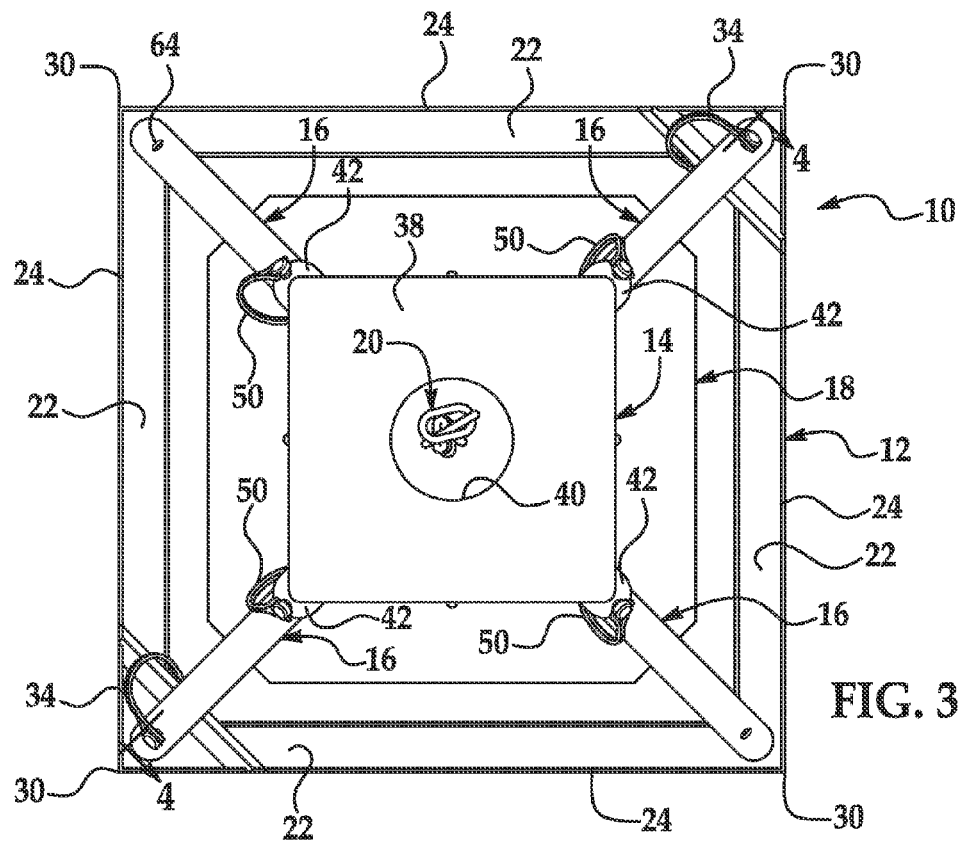
FIG. 3 is a top view of the roofing pull-test frame assembly.
Figure 4:
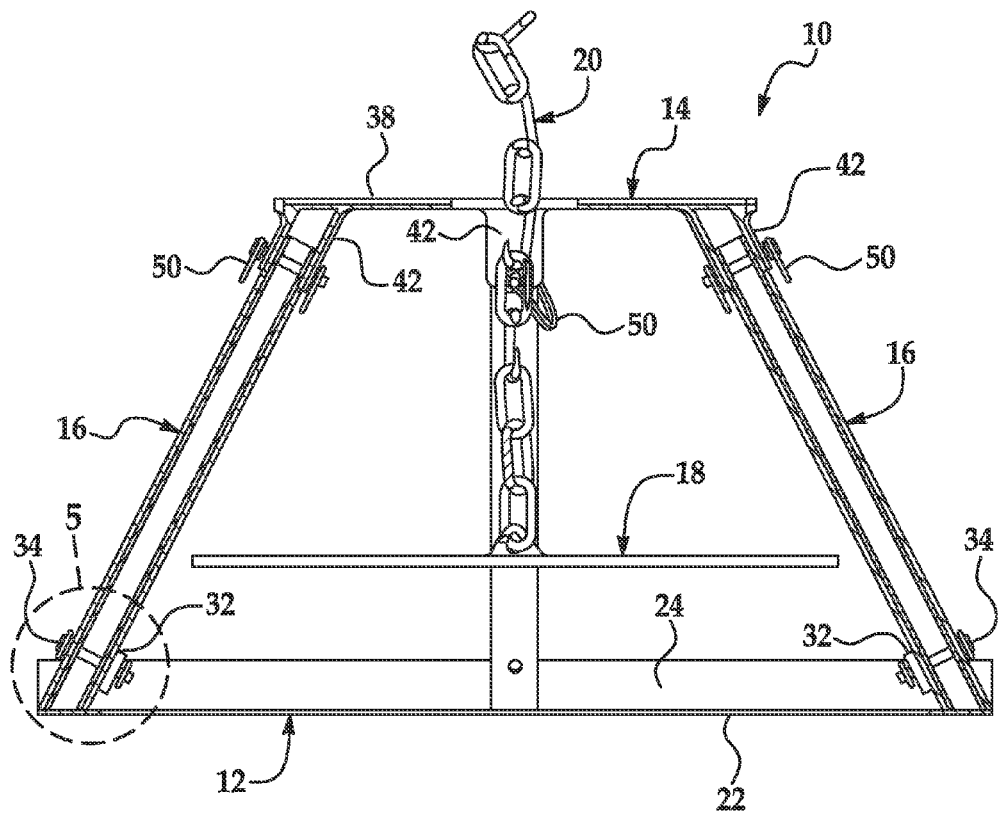
FIG. 4 is a sectional view taken at 4-4 in FIG. 3.
Figure 5:
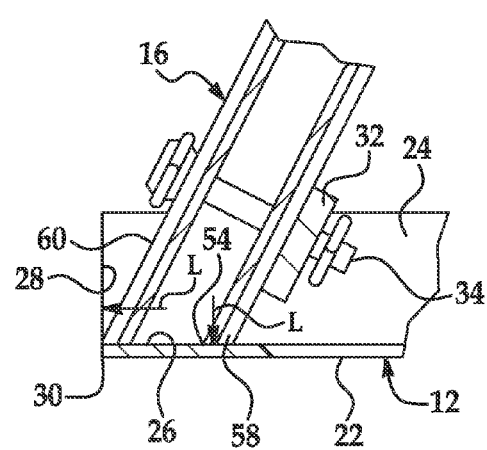
FIG. 5 is an enlarged view taken at circle 5 in FIG. 4.

The roofing pull-test frame assembly 10 is designed and constructed to transmit loads experienced during a pull-testing event more efficiently and effectively than previously-known pull-test frames. When the puller is actuated, for instance, loads are initially transmitted directly to the frame plate 14. From there, the loads are exerted to the legs 16 and to the base 12. Referring to FIG. 5, the loads L are transmitted between the legs 16 and base 12 via surface-to-surface abutment between the outside surface 60 and bracing surface 28, and via surface-to-surface abutment between the terminal end surface 58 and bracing surface 26. Hence, the base 12 endures the loads L in this way. Where the attachment structures 32 are provided, they serve merely to form a coupling between the base 12 and legs 16 and do not themselves substantially endure the loads L. It is possible, however, that some amount of load L is transmitted to the attachment structures 32 by the mere fact of their location; nevertheless, the design and construction of this coupling need not be intended to endure all of the loads L experienced. The attachment structures 32 are instead used as a coupling for carrying the roofing pull-test frame assembly 10 place to place on the exiting roof. This differs from some previously-known pull-test frames in which loads experienced during a pull-testing event are borne in part by pins and/or other mounting components—this has been shown to be unsuitable in some circumstances because the loads could require an undesirably large and bulky mounting.

The foregoing description is considered illustrative only. The terminology that is used is intended to be in the nature of words of description rather than of limitation. Many modifications and variations will readily occur to those skilled in the art in view of the description. Thus, the foregoing description is not intended to limit the invention to the embodiments described above. Accordingly the scope of the invention as defined by the appended claims.

What is claimed is:

1. A roofing pull-test frame assembly, comprising:
    a base for placement on a roof, the base having at least one wall with a bracing surface;
    a frame plate; and
    at least two legs extending between the base and the frame plate and supporting the frame plate above the base in assembly;
    wherein, in assembly and in use, loads experienced during a pull-testing event are transmitted from the frame plate, to the at least two legs, and to the at least one wall of the base where the at least two legs transmit the loads via surface-to-surface abutment with the bracing surface of the at least one wall, and wherein the base has an attachment structure extending from the at least one wall, at least one of the at least two legs is coupled to the attachment structure when the roofing pull-test frame assembly is assembled together, and at least one of the at least two legs lacks a coupling to the base and only maintains surface-to-surface abutment with the bracing surface via the transmitted loads.

2. The roofing pull-test frame assembly of claim 1, wherein the at least one wall of the base includes a first wall for placement directly on the roof and a second wall extending from the first wall, the bracing surface includes a first bracing surface of the first wall and a second bracing surface of the second wall, and the at least two legs transmit the loads via surface-to-surface abutment with the first bracing surface and with the second bracing surface.

3. The roofing pull-test frame assembly of claim 1, wherein the at least one of the at least two legs is coupled to the attachment structure via a clevis pin coupling.

4. The roofing pull-test frame assembly of claim 3, wherein loads experienced during a pull-testing event are not substantially transmitted to the coupling at the attachment structure and clevis pin coupling.

5. The roofing pull-test frame assembly of claim 1, wherein the at least two legs are coupled to the frame plate via clevis pin couplings.

6. The roofing pull-test frame assembly of claim 1, wherein the frame plate includes at least two sleeve structures extending therefrom, each of the at least two sleeve structures receiving one of the at least two legs in an overlapping arrangement when the roofing pull-test frame assembly is assembled together.

7. The roofing pull-test frame assembly of claim 1, further comprising a pull plate for attachment to the roof during a pull-testing event, and a chain attached to the pull plate and extendable through an opening in the frame plate.

8. A roofing pull-test frame assembly, comprising:
    a base for placement on a roof, the base having at least one wall with a bracing surface;
    a frame plate; and
    at least two legs extending between the base and the frame plate and supporting the frame plate above the base in assembly;
    wherein, in assembly and in use, loads experienced during a pull-testing event are transmitted from the frame plate, to the at least two legs, and to the at least one wall of the base where the at least two legs transmit the loads via surface-to-surface abutment with the bracing surface of the at least one wall; and
    wherein the at least one wall of the base includes a first bottom wall, a second bottom wall, a first side wall, and a second side wall, the first and second bottom and side walls come together at a corner of the base, and wherein, in assembly and in use, one of the at least two legs extends to the corner with a terminal end surface of the leg making surface-to-surface abutment with bracing surfaces of the first and second bottom walls and with an outside surface of the leg making surface-to-surface abutment with bracing surfaces of the first and second side walls.

9. A roofing pull-test frame assembly, comprising:
a base having a first bottom wall, a second bottom wall, a first side wall, and a second side wall, the first and second bottom and side walls come together at a corner of the base;
a frame plate; and
a leg extending between the base and the frame plate and supporting the frame plate above the base in assembly;
wherein, in assembly and use, the leg extends to the corner of the base and a terminal end surface of the leg makes surface-to-surface abutment with bracing surfaces of the first and second bottom walls and an outside surface of the leg makes surface-to-surface abutment with bracing surfaces of the first and second side walls;
wherein loads experienced during a pull-testing event are transmitted between the leg and the base via the surface-to-surface abutment between the terminal end surface of the leg and the bracing surfaces of the first and second bottom walls, and are transmitted between the leg and the base via the surface-to-surface abutment between the outside surface of the leg and the bracing surfaces of the first and second side walls;
wherein the base has an attachment structure extending between the first and second side walls, the leg is coupled to the attachment structure via a clevis pin coupling when the roofing pull-test frame assembly is assembled together.

10. The roofing pull-test frame assembly of claim 9, wherein loads experienced during a pull-testing event are not substantially transmitted to the clevis pin coupling.

11. The roofing pull-test frame assembly of claim 10, further comprising a pull plate for attachment to the roof during a pull-testing event, and a chain attached to the pull plate and extendable through an opening in the frame plate.

* * * * *